United States Patent [19]

Ando et al.

[11] Patent Number: 5,712,703
[45] Date of Patent: Jan. 27, 1998

[54] MEASURING SENSOR, DIFFUSE REFLECTANCE SPECTRUM MEASURING METHOD USING THE MEASURING SENSOR, AND EMULSION PRODUCTION APPARATUS

[75] Inventors: Hiroaki Ando; Haruhiko Masutomi; Kazuyoshi Ichikawa, all of Hino, Japan

[73] Assignee: Konica Corporation, Tokyo, Japan

[21] Appl. No.: 711,872

[22] Filed: Sep. 12, 1996

[30] Foreign Application Priority Data

Sep. 22, 1995 [JP] Japan ................................. 7-244005

[51] Int. Cl.⁶ ....................................................... G01J 3/42
[52] U.S. Cl. ........................... 356/319; 356/300; 356/302; 356/303
[58] Field of Search ................................. 356/319, 303, 356/326, 310, 302, 300, 325

[56] References Cited

U.S. PATENT DOCUMENTS

5,088,822  2/1992  Milosevic ................................. 356/319
5,283,624  2/1994  Tsukada et al. ......................... 356/319
5,636,015  6/1997  Imura et al. ............................. 356/319

*Primary Examiner*—Frank G. Font
*Assistant Examiner*—Reginald A. Ratliff
*Attorney, Agent, or Firm*—Frishauf, Holtz, Goodman, Langer & Chick

[57] ABSTRACT

A light spectrum measuring apparatus comprises a sensor case on which a window with a glass is provided; a light emitting member and a light receiving member both provided in the case so that light emitted from the light emitting member passes through the glass, is reflected from solution, returns in the case, and is received by the light receiving member, wherein the glass, the light emitting member and the light receiving member are arranged in such a positional relation that positive reflected light which is emitted from the light emitting member and directly reflected by the glass without proceeding in the solution, is not received by the light receiving member.

16 Claims, 12 Drawing Sheets

TIME ELAPSED AFTER SUPPLYING THE TOTAL AMOUNT OF DYES (TIME REQUIRED FOR SUPPLYING DYES IS THE SAME)

SPECTRAL CHANGES BASED ON ADSORBED AMOUNT OF DYES

EMULSION OF A

FIG. 17 (b)

EMULSION OF B

FIG. 18

SPECTRAL CHANGES BASED ON ADSORBED AMOUNT OF DYES 5,712,703

MEASURING SENSOR, DIFFUSE REFLECTANCE SPECTRUM MEASURING METHOD USING THE MEASURING SENSOR, AND EMULSION PRODUCTION APPARATUS

BACKGROUND OF THE INVENTION

The present invention relates to the production of liquid material having high sensitivity and high performance stability, a measuring sensor to enhance the production stability, a diffuse reflectance spectrum measuring method using the measuring sensor, and to an emulsion production apparatus to produce photographic emulsion.

For example, in many cases, silver halide grains in emulsion used for pigment or photosensitive material are handled as a dispersion solution. Their light adsorption behavior, light reflection, and light scattering behavior are very important for their purpose of use. Therefore, generally, the light absorption spectrum of dispersion solution, and the light absorption spectrum in their coated status are measured. The measurement of the spectrum of the dispersion solution is important, and various methods have been proposed.

In this connection, because the light diffusivity is very strong as features of the dispersion solution, the measurement of the spectrum of diffuse reflection light is more practical than that of the spectral absorption of the transmitted light. Generally, a measuring method of the spectrum of diffuse reflection light is conducted by a spectrophotometer having an integrating sphere. For example, this method is clearly described on page 108 of the group No. 1 of the first edition of (revised) "introduction of instrumental analysis" issued by Kagaku Dojin Co. However, this method requires the collection of a small amount of a liquid sample, and its spectrum changes during the collection time, when the spectrum changes in a short period of time due to chemical reaction, therefore, the correct spectrum can not be observed.

Accordingly, sometimes the circulation measuring method is used to measure the spectral changes caused by chemical reaction with high resolution power. This method is also described on page 108 of the above-described reference. In this method, the time resolution power of the measuring apparatus can be increased to several milliseconds and the spectral changes caused by the chemical reaction can be correctly tracked.

However, this method generates useless circulation time. In order to solve also this point, the size of the apparatus becomes correspondingly larger, and it is difficult to use the apparatus easily. For example, when dispersion solution such as silver halide grains in emulsion is adjusted, in many cases, a considerably large reaction tank is used. In order to track changes of the spectral absorption while adjusting the dispersion solution, it is necessary to circulate the solution. For this purpose, the increase of a burden, such as a request for providing new pipes, is unavoidable.

Spectral sensitization is the essential technology in the production of silver halide emulsion. Whether or not the spectral sensitization can attain the initial purpose, largely depends on how sensitizing dye is adsorbed. As a method for judging the condition of adsorption, the following methods are commonly used: a method for measuring the spectrum under the condition that the dye is coated on emulsion or a base; or a method for checking the photographic performance. If the adsorption condition of the dye can be checked during the spectral sensitization process, corrective actions can be quickly conducted in case of troubles of the apparatus during production. In many cases, sensitizing dyes are used together in spectral sensitization. If another sensitizing dye can be added while checking the adsorption condition of one sensitizing dye, it can be expected that the sensitivity of spectral sensitization is increased or its storage property is improved, by controlling the method of addition of the sensitizing dye.

However, in many cases, the time from addition of sensitizing dye to silver halide emulsion to the completion of adsorption of sensitizing dye, requires only several minutes. Accordingly, when the adsorption condition of the sensitizing dye is checked by a spectrum measuring apparatus provided separately from the emulsion charging apparatus, time is wasted, and thereby, practical data of adsorption condition of dyes can not be obtained. In such a conventional emulsion production apparatus, the following can not be attained: the spectral sensitization process is highly controlled while monitoring the adsorption of sensitizing dye, and silver halide photographic emulsion with high sensitivity and excellent storage stability, is produced; and the reproducibility of the spectral sensitization for all production lots is enhanced.

SUMMARY OF THE INVENTION

The present invention is achieved in view of the foregoing description. An object of the present invention is to provide a measuring sensor to easily measure the spectrum of reflected light of liquid material in real time, and a measuring apparatus using the measuring sensor. Another object of the present invention is to produce silver halide emulsion with high sensitivity and excellent storage stability with the use of the above measuring apparatus, and to provide an emulsion production apparatus which can enhance the reproducibility of spectral sensitization for all production lots.

In order to solve the above-described problems and to attain the objects, the measuring apparatus of the invention comprises: a light projection means to emit light onto liquid material; a light receiving means to receive reflected light from the liquid material; and a measuring means to measure the spectrum of the reflected light in real time. As described above, when emitting the light onto the liquid material, receiving the reflected light from the liquid material, and measuring the spectrum of the reflected light in real time, data can be quickly obtained without manually receiving the experimental data.

In the invention, it is preferable that the reflected light is diffusive reflection light. As described above, because the reflected light is diffusive reflection light, and for example, the diffusive reflection light reflected by the measuring object is received and measured without receiving the reflected light by a light transmitting window provided in the sensor unit, the spectrum analysis can be positively carried out.

In the invention, it is preferable that the liquid material is photosensitive material in the spectrum sensitization process. As described above, because the liquid material is the photosensitive material in the spectrum sensitization process, the behavior in the spectrum sensitization process of the emulsion can be recognized, which could not be conducted before now.

In the invention, it is preferable that the light projecting means and light receiving means are composed of optical fiber; the optical fiber is provided in a sensor unit located in a case having a light transmitting window; and the sensor unit is provided in direct contact with the liquid material in the production line of the liquid material. In this manner, because the optical fiber is provided in the sensor unit located in the case having the light transmitting window, and the sensor unit directly contacts with the liquid material in the production line of the liquid material, it is not necessary to collect a portion of a liquid sample, and therefore, simple and real time measurement can be achieved.

In the invention, it is preferable that the light projection means and light receiving means are composed of a plurality of optical fibers; the optical fibers are integrally bundled; the bundled optical fibers are provided in the sensor unit located in the case having the light transmitting window; and a measuring system to take out the liquid material from the production line of the liquid material is provided; and the sensor unit is provided for direct contact with the liquid material in the measuring system. In this manner, because the optical fiber is provided in the sensor unit located in the case having the light transmitting window, and the sensor unit is in direct contact with the liquid material in the measuring system to take the liquid material from the production line of the liquid material, it is not necessary to collect a portion of a liquid sample, and therefore, simple and real time measurement can be achieved.

In the invention, it is preferable that: the optical fiber is arranged inside the sensor unit; and the distance "d" from the leading edge of the optical fiber to the contact portion with the light transmitting window, to which the central axis of the optical fiber is extended, is determined and set according to the following relational expression, $$d \geq a/\sin \theta \{[\cos \beta/\cos (\theta+\beta)]-\cos \theta\}$$

where, a . . . an effective diameter of the optical fiber

θ . . . an expansion angle of the luminous flux from the optical fiber

β . . . a angle formed by the central axis of the optical fiber and the light transmitting window.

In this manner, when a effective diameter of the optical fiber, an expansion angle of the luminous flux, a angle formed between the central axis of the optical fiber and the light transmitting window, and the distance from the leading edge of the optical fiber to its contact portion with the light transmitting window, to which the central axis of the optical fiber is extended, are set, the size of the sensor unit can be reduced, and it is not necessary to collect a portion of a liquid sample, therefore, simple and real time measurement can be achieved.

In the invention, it is preferable that the light transmitting window is made of glass. In this manner, when the light transmitting window is made of glass, the window is prevented from softening even when the temperature of the liquid material, the spectrum of which is to be measured, is high.

In the invention, it is preferable that the adsorption condition of the sensitizing dye on the silver halide grains is measured in the sensitization process of the photosensitive emulsion. In this manner, when the adsorption condition of the sensitizing dye on the silver halide grains is measured in the sensitization process of the photosensitive emulsion, the behavior of the emulsion in the spectral sensitization process can be recognized, which has not been conducted up to now.

In the invention, it is preferable that: the measuring sensor described above is provided in the production line of the emulsion; and an addition means to add additives at on-line, while continuously monitoring and controlling the adsorption condition of the sensitizing dye onto the silver halide grains in the emulsion, obtained from the measuring sensor, is provided. In this manner, when additives are added at on-line while continuously monitoring and controlling the adsorption condition of the sensitizing dye, the production of silver halide emulsion with high sensitivity and excellent storage stability can be achieved, and the reproducibility of the spectral sensitization for all production lots can be enhanced.

DETAILED EXPLANATION OF THE INVENTION

Next, a measuring sensor, a measuring method of diffuse reflectance spectrum using the measuring sensor, and an emulsion production apparatus, of the present invention will be described.

initially, an example of a measuring sensor of the present invention is shown in FIG. 1(a). In FIG. 1(a), the measuring sensor A includes a sensor unit B, a measuring means C, and a light source D, and, for example, it is used in a spectral sensitization process when an emulsion of liquid material is produced. The sensor unit B is structured in such a manner that a ring 3, fixing a light transmitting window 2, is fixed on an opening 6a of a cylindrical case 6 by set screws 1. As the light transmitting window 2, glass or transparent synthetic resins, with sufficient light transmitting property, can be appropriately selected for use. However, when the temperature of liquid material, the spectrum of which is to be measured, is high, glass is the most preferable material as the material applied for the light transmitting window 2, because sometimes a resin window is softened due to high temperature.

A ring-slot 4 is formed in the opening 6a of the case 6, and an O-ring 5 is inserted into the ring-slot 4. That is, the light transmitting window 2 and the opening 6a of the cylindrical case 6 are in tight contact with each other by the O-ring 5, thereby, no liquid can enter into the inside of the cylindrical case 6 even when the entire light transmitting window 2 is immersed in the emulsion of the liquid material.

An optical fiber probe 7 is inserted into the case 6. As shown in FIG. 1(b), the optical fiber probe 7 is formed in such a manner that many light projection optical fibers 7a necessary for the light absorption spectrum measurement, and many light receiving optical fibers 7b are bundled in equal numbers. Accordingly, a light projection range coincides with a light receiving range. The light projection optical fibers 7b structure a light projection means to emit the light onto the emulsion. The light receiving optical fiber 7b structures a light receiving means to receive diffuse reflection light from the emulsion. This unit is structured such that light is emitted from the optical fiber probe 7; the light is projected on the emulsion through the light transmitting window 2; and the diffuse light reflected from the emulsion returns again to the light receiving optical fibers of the optical fiber probe 7 through the light transmitting window 2.

The optical fiber probe 7 is connected to a spectrophotometer 11. The spectrophotometer 11 measures the diffuse reflectance spectrum, and constitutes the measuring means C which measures the diffuse reflectance spectrum in real time from the diffuse reflection light obtained from the light receiving means. The optical fiber probe 7 is fixed in the case 6 by a set screw 8. Numeral 9 is a hole for the set screw formed in the case 6.

Figure 2:
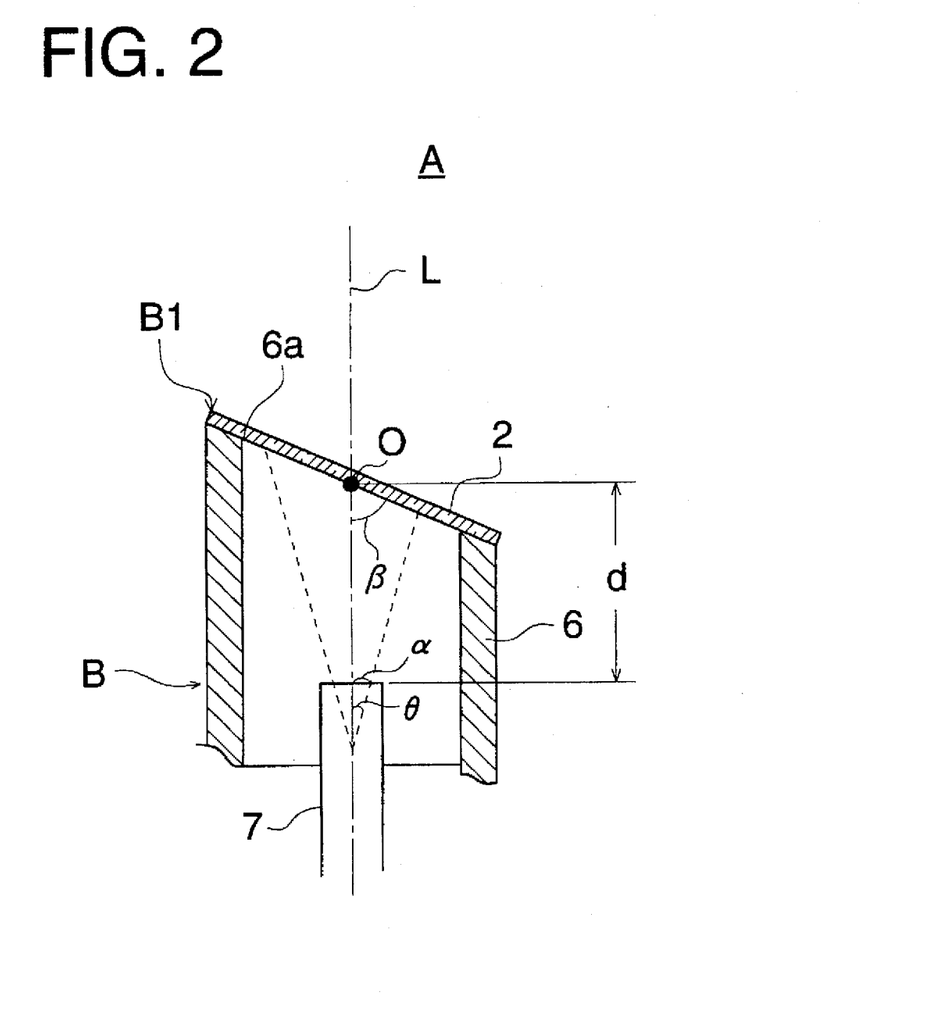
FIG. 2 is a view showing the structure of a sensor unit of the measuring sensor.

In the measuring sensor A, the optical probe 7 is arranged in the sensor unit B as shown in FIG. 2. The distance "d" from the leading edge of the optical fiber to the contact portion with the light transmitting window, to which the central axis of the optical fiber is extended, is determined and set according to the following relationship, $$d \geq a/\sin\theta \{[\cos\beta/\cos(\theta+\beta)] - \cos\theta\}$$

where, a: the effective diameter of the optical fiber

θ: the expansion angle of the luminous flux from the optical fiber

β: the angle formed by the central axis of the optical fiber and the light transmitting window For example, when the effective diameter "a" of the optical fibers of the light projecting optical fibers 7a and the light receiving optical fibers 7b=2 mm, the expansion angle θ of the luminous flux from the optical fibers=10°, the angle β formed by the central axis of the optical fiber and the light transmitting window=60°, then, the following result is obtained, $$\text{distance "d"} \geq 2/\sin 10° \{[\cos 60°/\cos 70°] - \cos 10°\} \geq 11.4 \text{(mm)}$$

The distance "d", for example, is preferably longer than about 11.4 mm, and when the distance "d" is shorter than that value, the positive reflection light from the light transmitting window 2 directly enters into the light receiving optical fiber 7b, thereby a correct diffuse reflection spectrum can not be measured. The smaller the angle β, formed by the central axis of the optical fiber and the light transmitting window, is, the smaller the distance "d" is. However, since the leading edge B1 of the sensor unit B projects forward, and the surface area of the light transmitting window 2 becomes large, the size of whole sensor unit B becomes larger. When the distance "d" is too large, the luminous flux from the optical fiber is directly projected on the cylindrical portion of the case 6, and the irradiation light is disturbed, and consequently the size of the sensor unit B is increased. Accordingly, the distance "d" can be appropriately selected to be within the range, satisfying the above-described range, and it is preferable that the distance "d" is not too large.

The measuring sensor A can be used within the range of 0° to 100° C., and specifically, it is preferable that the sensor A is used within the range of 10° to 80° C. because influence due to the temperature is less and a more highly accurate measurement can be achieved. Wavelengths of light in which the light transmittance is larger within the range of the wavelength, for example, from 190 nm to 800 nm of ultraviolet light, visible light, and infrared light, is used in this invention.

As a light source D, a tungsten lamp, a xenon lamp, a mercury lamp, etc., are used when measuring the region from visible light to infrared light, and a lamp which emits light having wavelengths of 400 through 800 nm, is not specifically limited. When the ultraviolet light region is measured, an ultraviolet ray generation apparatus is used. Further, excessive light may also be cut by filters. For example, when the measurement is conducted in the spectral sensitization process during the production of emulsions, it may be preferable to use a filter to cut unnecessary light deteriorating the emulsion.

As optical fibers of the optical fiber probe 7, for example, Y-type fibers by Ohtsuka Electronics Co., can be used. The light projection and light receiving fibers are respectively composed of several tens of finer fibers, and are compact and easily manipulated. These optical fibers can measure the reflection spectrum from the liquid surface independently. However, in the chemical reaction tank, generally, the emulsion is vigorously stirred, and the surface of the emulsion always changes due to flow.

Accordingly, only mounting the fibers above the liquid surface leads to the projection light being greatly affected by variations of the positive reflection light which is directly reflected from the interface between liquid and air. Therefore, it is difficult to correctly measure the diffuse reflection spectral changes of the emulsion itself. When the leading edge of the fiber probe is immersed in the emulsion, the projection light is not affected by variations of the positive reflection light. However, by that measuring method, the projection light is collectively irradiated onto dispersoid existing on the leading edge portion of the fiber probe. Accordingly, when the material which is weak against the light, is a dispersion solution, the dispersion solution is deteriorated during the measurement of spectrum, resulting in an incorrect spectrum measurement. Even if the spectrum can be measured, it is different from the so-called diffuse reflectance spectrum. This is clear when referring to page 17 of "Spectrum Measurement and Spectrophotometer" (written by Kazuo Shibata and published by Kodansha).

Figure 3:
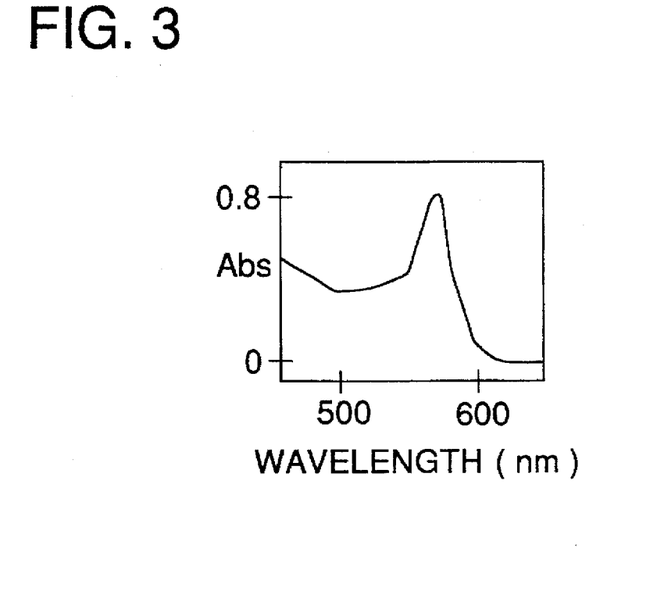
FIG. 3 shows a diffuse reflectance spectrum of a dispersion solution measured by using a normal integral sphere.
Figure 4:
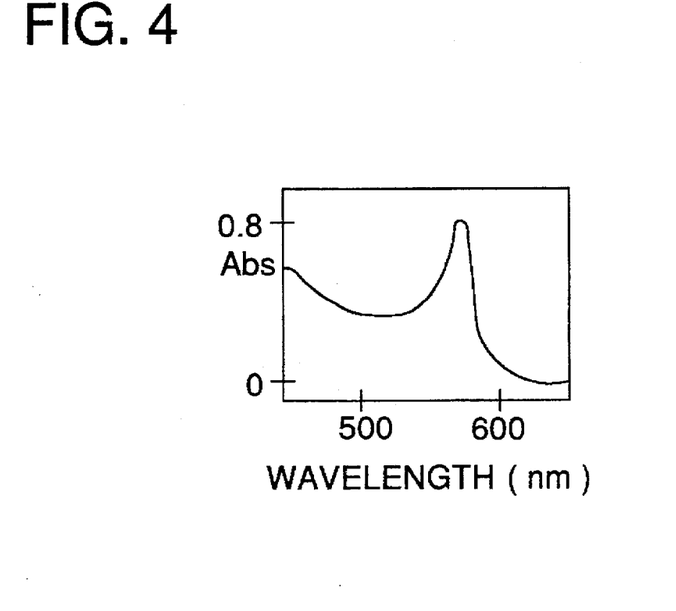
FIG. 4 is a spectrum obtained by a combination of a Y-type probe of the present invention and a MCPD-1000 made by Ohtsuka Electronics Co.
Figure 5:
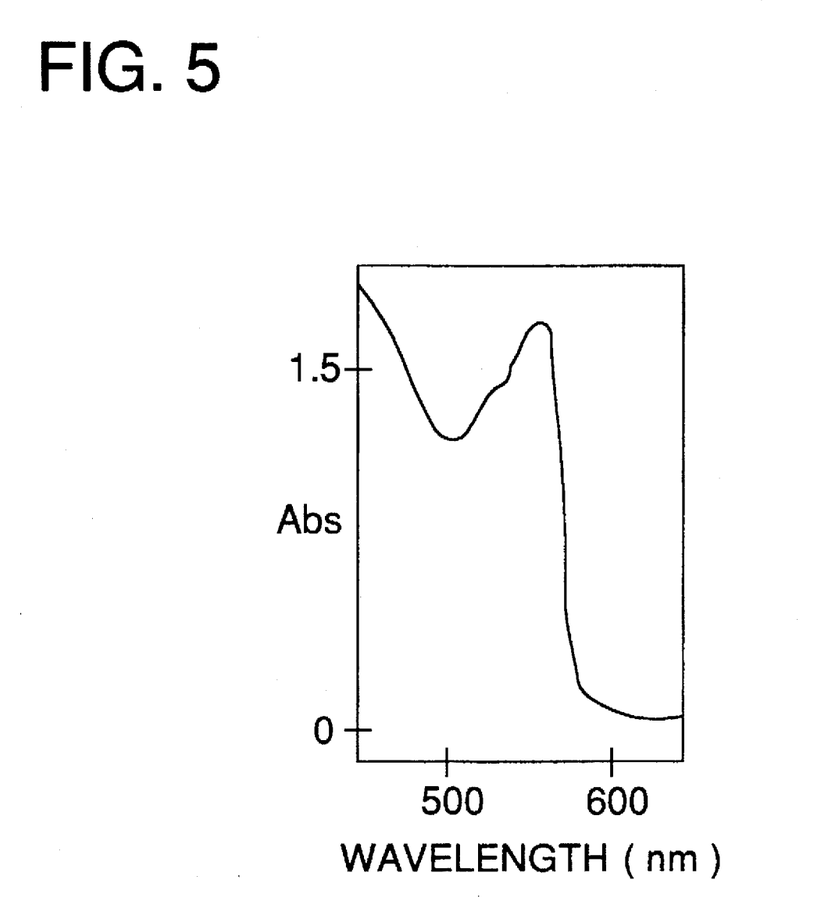
FIG. 5 is a spectrum obtained when the leading edge of the Y-type fiber is immersed in the emulsion, without using the measuring sensor.

Further, to more clearly understand the above description, the spectrums measured by various kinds of methods are shown in FIGS. 3 through 5. The "Abs.", shown by the vertical axis of the spectrum, is defined by the following relationship:

Abs.=−log 10 (the intensity of the diffuse reflection light from the sample/the intensity of the diffuse reflection light from the white reference plate used as the reference)

Alternatively, the vertical axis may be expressed by the following relationship:

R (%)=(the intensity of the diffuse reflection light from the sample/the intensity of the diffuse reflection light from the white reference plate used as the reference)

FIG. 3 is the diffuse reflectance spectrum measured by the normal integral sphere. FIG. 4 is the spectrum obtained by a combination of the present invention, the Y-type probe and MCPD-1000, produced by Ohtsuka Electronics Co. FIG. 5 is the spectrum obtained by immersing the leading edge of the Y-type fiber probe into the emulsion, without using the measuring sensor of the present invention. The spectrums shown in FIGS. 3 and 4, have very similar waveforms, however, the spectrum shown in FIG. 5 has a clearly different waveform from the other two. This means that the present invention is effective for the measurement of the normal diffuse reflectance spectrum.

Figure 6:
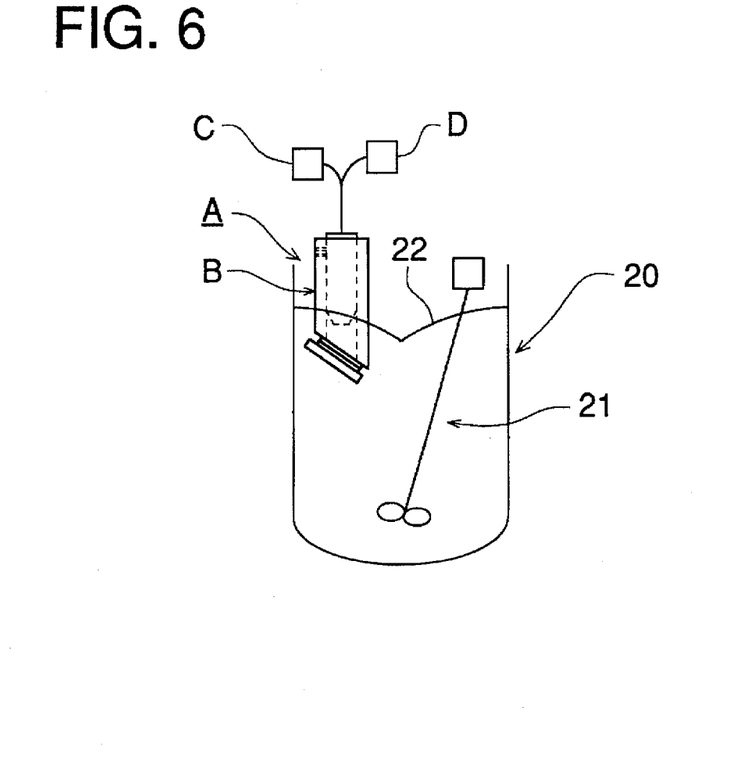
FIG. 6 is a view showing a mounting condition of the measuring sensor.

FIG. 6 shows how the measuring sensor is used. A reaction tank 20 is arranged in the spectral sensitization process of the liquid material, and the liquid material in the reaction tank is stirred by a stirring unit 21. In the liquid material, a sensor unit B of a measuring sensor A is immersed into the liquid from above, and a light transmitting window 2 portion is positioned below the liquid surface 22. A light source C and a measuring means D, including a detector and a data processing section, are connected to the sensor unit B. The light source C and the measuring means D may be a combination appropriate for the measurement of the spectral absorption.

Figure 1:
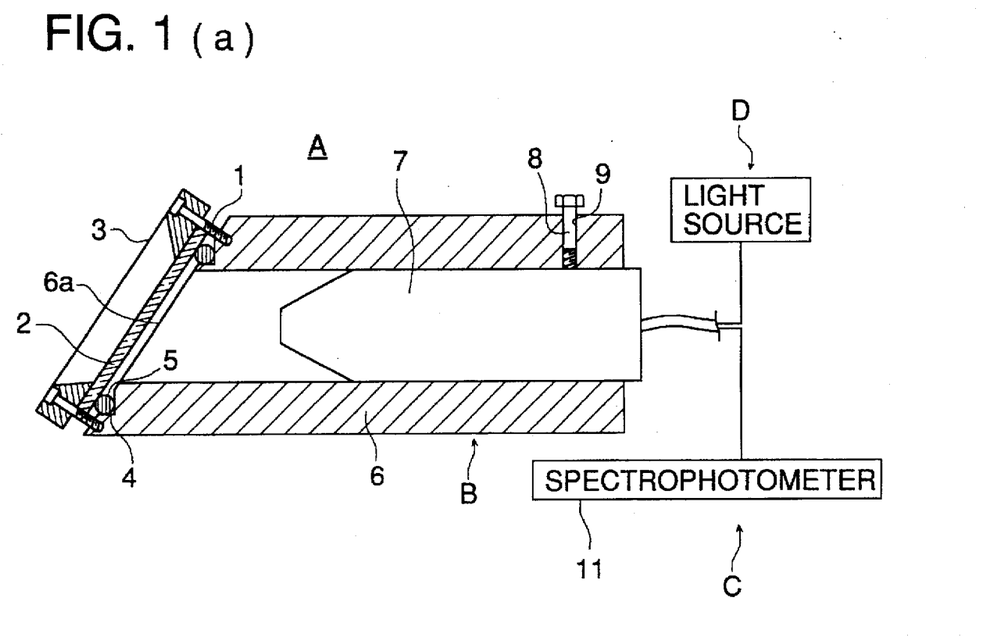
FIGS. 1(a) and 1(b) are views showing the structure of a measuring sensor.

It is necessary that the light transmitting window 2 of the sensor unit B is structured so that the positive reflection light from the light projecting optical fibers 7a does not return to the light receiving optical fibers 7b. In FIGS. 1 and 2, the light transmitting window 2 is at an angle to the central axis of a cylindrical case 6. However, even if such a structure is not adopted, any structure in which the positive reflection light does not return to the light receiving optical fibers 7b, may be allowed. Further, the material of the light transmitting window is not necessarily limited to silica glass.

It is required that optical fibers can be fixed inside the sensor unit B. It is preferable that the light projecting and light receiving optical fibers are fixed so that they exclude positive light, and can measure mainly the diffusive reflection light. Further, when the position of the light projecting optical fibers is adjusted and an area of light irradiating the dispersion solution, is adjusted, it prevents that light intensively irradiates only a certain area of the dispersion solution, thereby the diffuse reflectance spectrum of the dispersion solution, which is weak against light, can be measured. Although the position is adjusted by set screws in this example, the present invention is not limited to this structure.

In the present invention, the light transmitting window 2 of the sensor unit B is used while being immersed in the dispersion solution, and it may be structured so that the light transmitting window 2 is tightly contacted with the case 6 to seal it from the dispersion solution.

Figure 7:
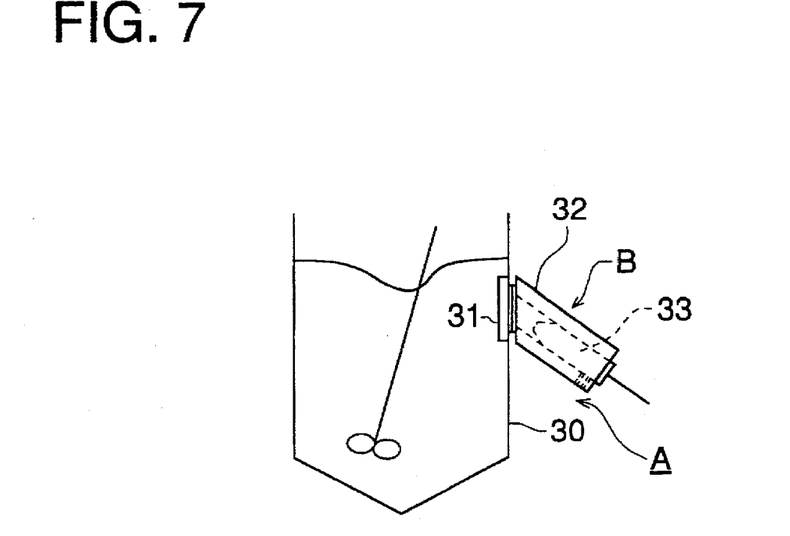
FIG. 7 is a view showing a mounting condition of the measuring sensor of another example.

Further, the measuring sensor A can also be positioned as shown in FIG. 7. A light transmitting window 31 is provided in a portion below the liquid surface on a side wall of the reaction tank 30, and an integrated type optical fiber probe 33 provided inside the case 32 can be positioned opposite to the light transmitting window 31.

Figure 8:
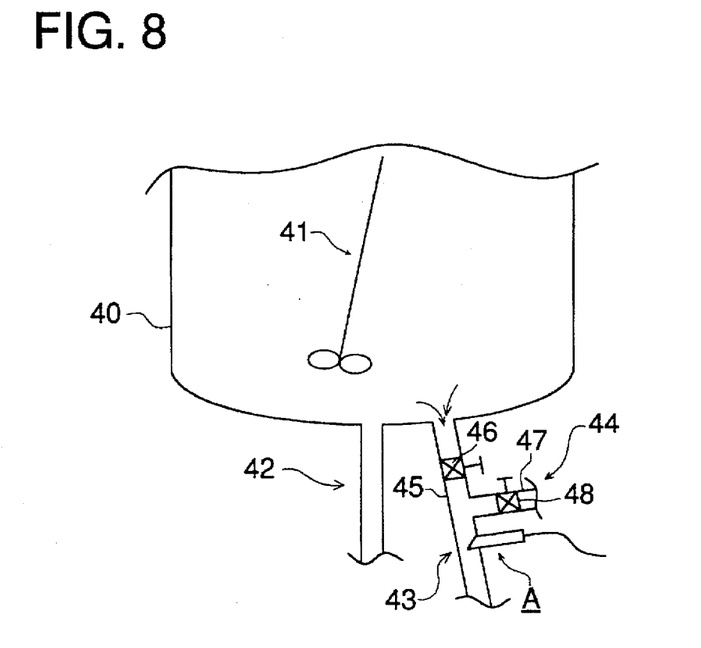
FIG. 8 is a view showing a mounting condition of the measuring sensor of still another example.
Figure 9:
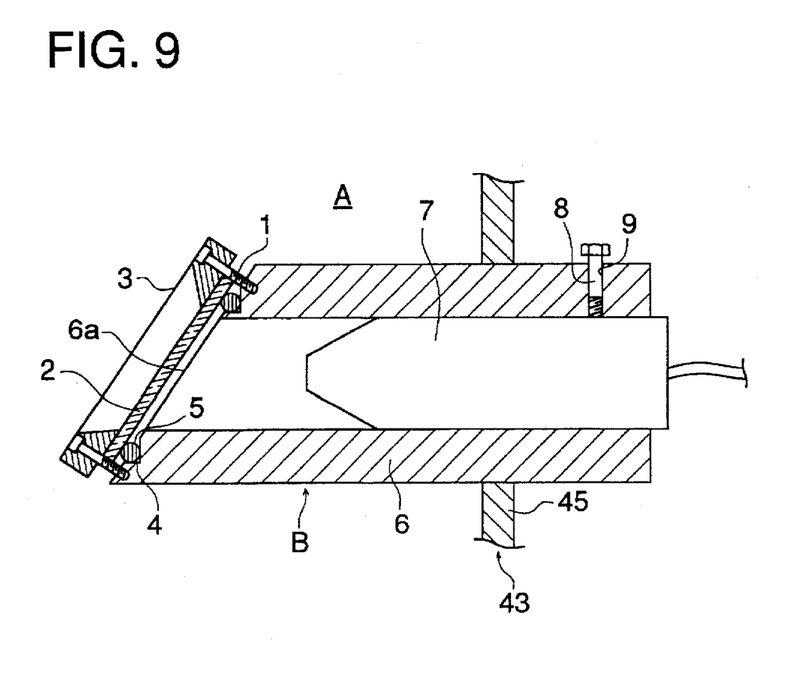
FIG. 9 is a view showing the structure of an example in which the measuring sensor is mounted in a measuring system.

Furthermore, the measuring sensor A can also be positioned as shown in FIGS. 8 and 9. A stirring unit 41 to stir the liquid material during its production, is positioned inside the reaction tank 40, and a delivery system 42 to deliver the produced liquid material, and a measurement system 43 to sample the solid material from the liquid material production line, are provided below the bottom of the reaction tank 40. A washing system 44 is provided in the measurement system 43. A valve 46 is provided in a sampling pipe 45 of the measurement system 43, and the measuring sensor A as shown in FIGS. 1 and 2 is provided downstream of the valve 46. A valve 48 is provided in a washing pipe 47 of the washing system 44, and the washing pipe 47 is connected to the sampling pipe 45 upstream of the measuring sensor A.

When the valve 46 is opened during the spectrum measurement, the liquid material flows from the sampling pipe 45 and arrives at the leading edge of the probe portion of the measuring sensor A. There, the liquid material is directly irradiated by light, and the diffuse reflectance spectrum is measured from the diffuse reflection light from the liquid material in real-time. When the measurement is completed, the valve 46 is closed, the valve 48 of the washing system 44 is opened, and warm pure water is supplied from the washing pipe 47 for washing the measuring sensor A.

Figure 10:
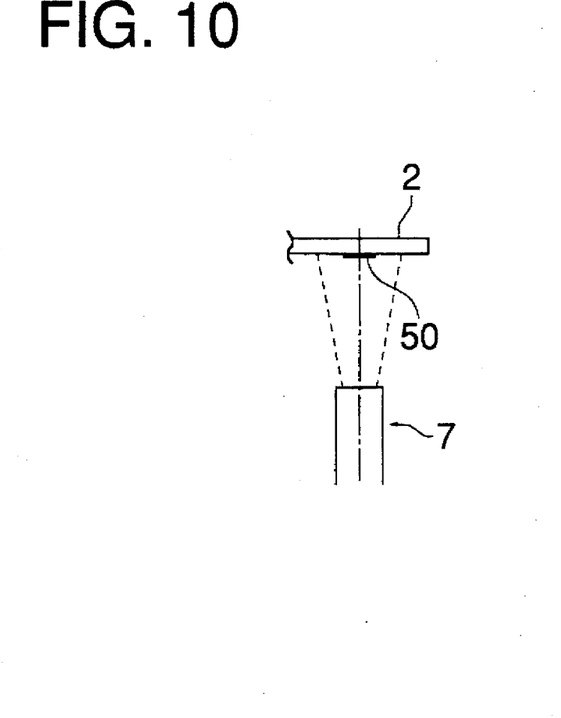
FIG. 10 is a view showing the structure of another example of the measuring sensor.
Figure 11:
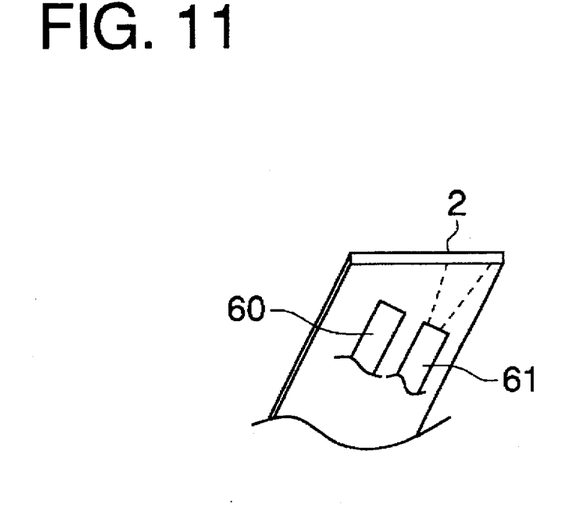
FIG. 11 is a view showing the structure of still another example of the measuring sensor.

In this connection, in the present invention, a black body 50 may be provided on the central portion of the light transmitting window 2, inside the case 6 of the sensor unit B, so that a portion on which the positive reflection light is irradiated, absorbs the light, and other portions do not absorb the diffusive reflection light. Specifically, an integral sphere may be provided inside the case 6 of the sensor unit B. Further, as shown in FIG. 11, light projecting optical fibers 60 and light receiving optical fibers 61, which are required for light absorption spectrum measurement, may be respectively provided separately inside the case 6 of the sensor unit B.

Figure 12:
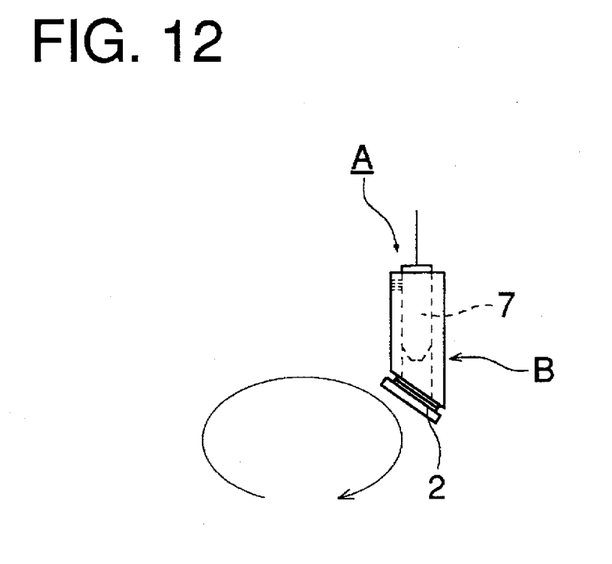
FIG. 12 is a view showing the structure of another example of the measuring Sensor.
Figure 13:
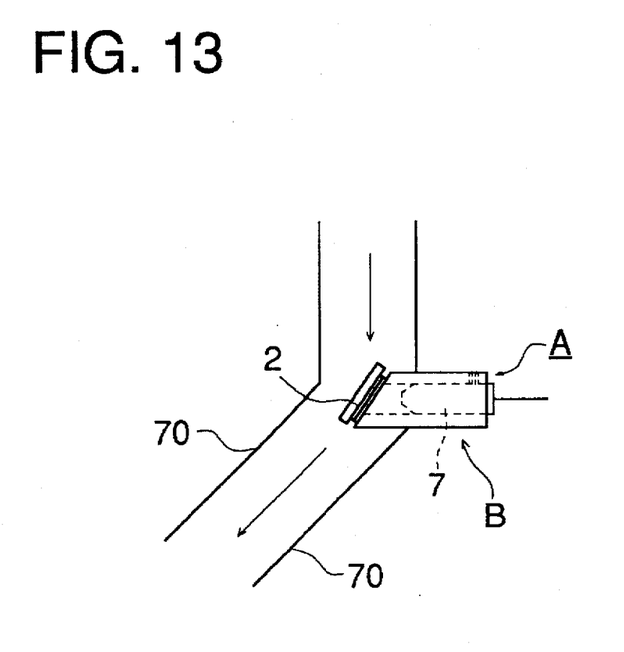
FIG. 13 is a view showing the structure of another example of the measuring sensor.

When the measuring sensor A is used, for example, in the spectrum sensitization process in the production of emulsion of the liquid material, the measurement accuracy is increased further in the measurement under flowing conditions rather than under static conditions. Further, the measurement accuracy is also increased when the sensor A is used under conditions that the emulsion does not stay near the light transmitting window 2. Therefore, as shown in FIG. 12, when the emulsion is stirred, the liquid is caused to flow against the light transmitting window 2 of the measuring sensor A. Alternatively, as shown in FIG. 13, a baffle plate 70 is provided so that the liquid flows against the light transmitting window 2 of the measuring sensor A.

The spectrophotometer 11 used in the present invention may be either a single-beam type or a double-beam type. However, for the purpose of tracking the chemical reaction, it is preferable that the spectrophotometer 11 has a high time-resolution power.

Further, in the measurement using the measuring sensor A, there may be cases in which the measuring sensor A may be immersed in the reaction tank, and cases in which it may not be immersed in the tank. The former case corresponds to a case, in which the emulsion has low sensitivity, such as the printing photosensitive material, or similar material, and in which the influence due to fogging is not problem, when the amount of light can be adjusted so that light from the light source does not adversely affect the reaction of the liquid material, and the adsorption speed of the sensitizing dye is measured in a laboratory or the like. On the other hand, in cases in which the emulsion is highly sensitive, such as ISO sensitivity 100 negative film, and the influence due to fogging becomes a problem, it may be preferable not to immerse the sensor in the reaction tank.

[EXAMPLE 1]

Figure 14:
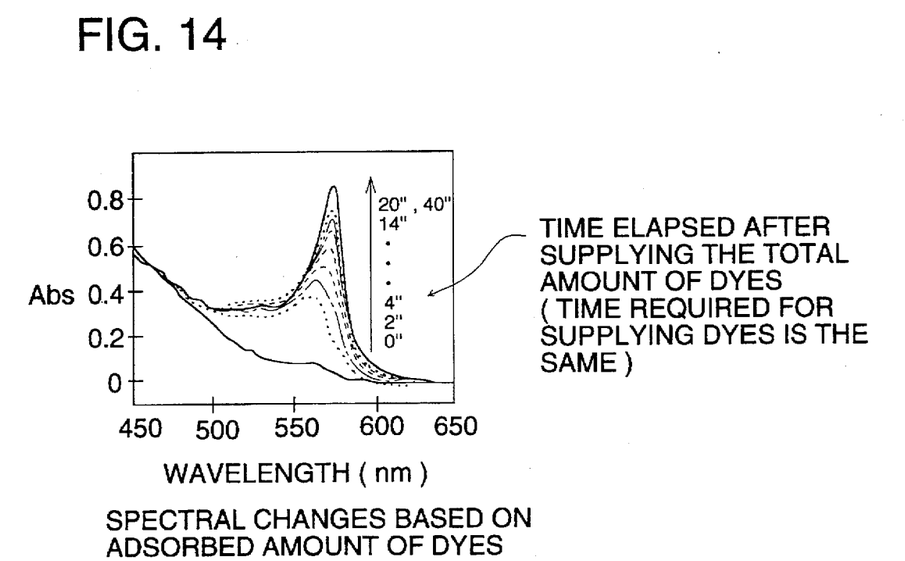
FIG. 14 is a view showing diffuse reflectance spectra.

Actually, the spectral sensitization in photographic photosensitive material will now be shown as an example. In FIG. 14, changes of the diffuse reflection spectra obtained in the present invention are shown. The spectral sensitization process is a process in which dyes, called as sensitizing dyes, are added into the dispersion solution of silver halide grains, and are adsorbed on the silver halide grains. When the sensitizing dye is adsorbed on the silver halide grains, its diffuse reflectance spectrum is changed. However, its adsorption reaction occurs very quickly in many cases, and therefore, conventionally the reaction can not be tracked by the change of the reflection spectrum. Sometimes a plurality of sensitizing dyes are used at the same time, and their dye adsorption behavior can be recognized by the present invention. Thereby, timing to add another sensitizing dye, which is used together, can be accurately controlled.

Figure 15:
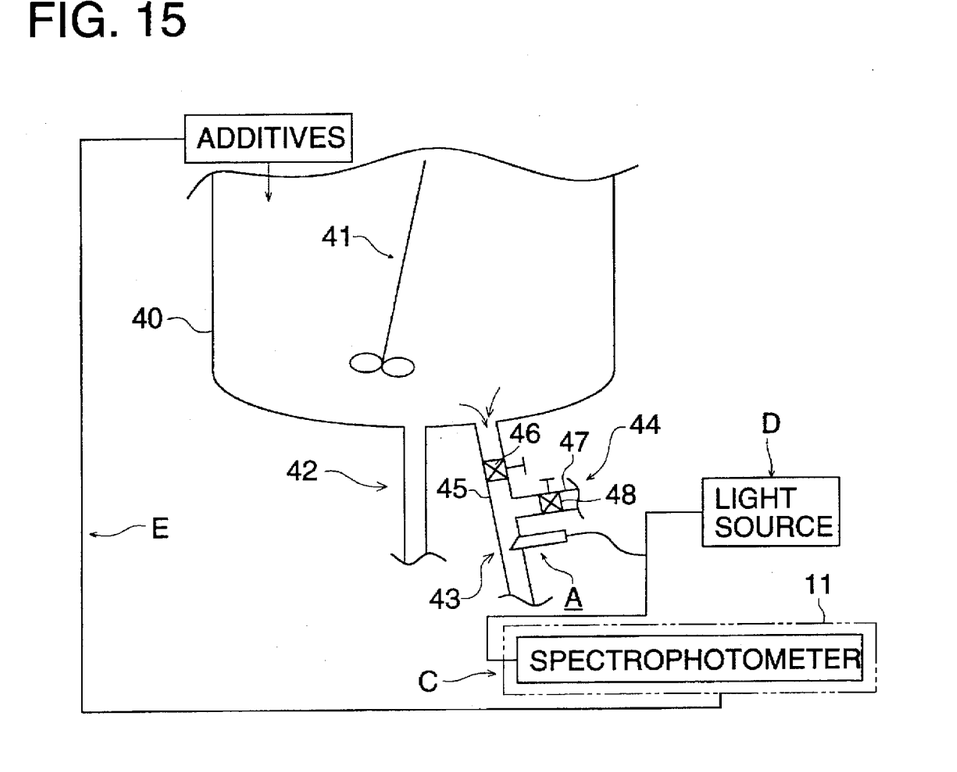
FIG. 15 is a view showing the structure of an emulsion production apparatus.

Next, an example of an emulsion production apparatus will be described. As shown in FIG. 15, the emulsion production apparatus is provided with a measuring sensor A in the emulsion production line, and with an addition means E which continuously monitors sensitizing dye adsorption conditions onto silver halide grains in the emulsion, obtained by the measuring sensor A, and adds additive agents one-line while controlling the adsorption condition.

In this emulsion production apparatus, because members denoted by the same numbers as in FIG. 8 are structured in the same way as described before, redundant explanation is omitted. As shown in FIG. 9, the measuring sensor A is provided in the measurement system 43, and is structured such that the sensor A is not vibrated during passage of emulsion. The measuring sensor A is structured as shown in FIGS. 1 and 2.

Generally, in order to measure the spectrum, light is irradiated onto the emulsion, and the reflected light is measured. Originally, silver halide emulsion is quite sensitive to light, and converted into blackened silver when the irradiation light is too intensive. However, when the amount of light irradiated onto a predetermined amount of silver halide emulsion is lower than a predetermined value, the generation of blackened silver is suppressed and the spectrum can be effectively measured.

Specifically, the condition changes depending on the composition, crystal habit, grain diameter, and sensitivity of silver halide, however, the optimum value of the flow rate of the emulsion and the amount of irradiated light are experimentally determined. However, it is desired that the emulsion used in the measurement is not mixed into the original emulsion. Accordingly, when the flow rate is too high, an ineffective amount of the emulsion is increased, therefore, the flow rate is preferably between 0.1 ml/min and 10000 ml/min, and more preferably, between 1 ml/min and 1000 ml/min. Because it is not preferable that the sensor unit B of the measuring sensor A is dried while the emulsion adheres on the sensor unit B, the sensor unit B is washed.

Even when light is irradiated on the emulsion for the spectrum measurement, it is not necessary to discard the emulsion when there is no problem in its performance. Accordingly, as shown in FIG. 6, it is allowed to directly introduce the sensor unit B of the measuring sensor A into the reaction tank. In this case, it is necessary to immerse the glass window into the emulsion. Alternatively, as shown in FIG. 7, a glass window may be provided on the side portion of the reaction tank, and the sensor unit B may be provided opposite to the glass window.

As a spectrum measuring apparatus, an apparatus having comparatively high time-resolution power is desirable. For example, MCPD-1000 made by Ohtsuka Electronics Co., can measure the spectrum, at least, in units of seconds, and is appropriate for the spectrum measuring apparatus used in the present invention.

Of course, when the dye adsorption condition is monitored by the spectrophotometer 11, spectral absorption patterns are stored in a computer, and the spectral sensitization process can therefore be controlled. That is, when the wavelength of the spectrum in the process is within the range of the reference, the production sequence can advance from the spectral sensitization process to the next process. However, when the wavelength of the spectrum does not satisfy the above condition, remedies can be taken at this point. When trouble is not found at this point, the following processes can not be used effectively, resulting in the possibility of major damage.

Further, other dyes or photographic additive agents can also be added while the dye adsorption conditions are being monitored. When several sensitizing dyes are used together, and during adsorption of one dye, when addition of the other sensitizing dye is effective, then the other dye may be added at the point of time when the wavelength of spectral absorption is constant. Because the dye adsorption process is influenced by, for example, emulsion temperature or the flow rate of additional dye, it is desirable that these factors can be controlled.

[EXAMPLE 2]

The following sensitizing dye 1 is added and the change of spectrum due to dye adsorption is measured during the spectral sensitization.

Figure 16:
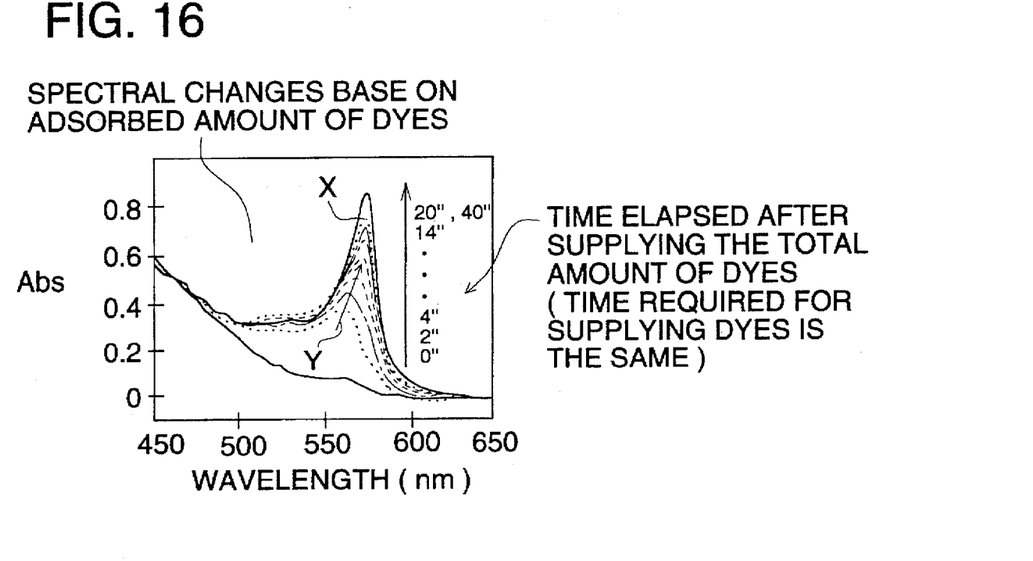
FIG. 16 is a view showing another example of diffuse reflectance spectra.
Figure 17A:
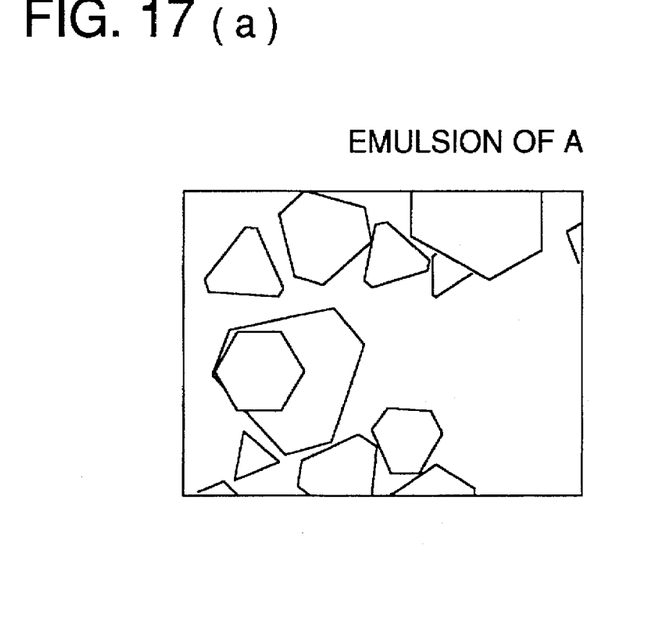
FIGS. 17(a) and 17(b) are conceptual views showing emulsion grains.
Figure 17B:
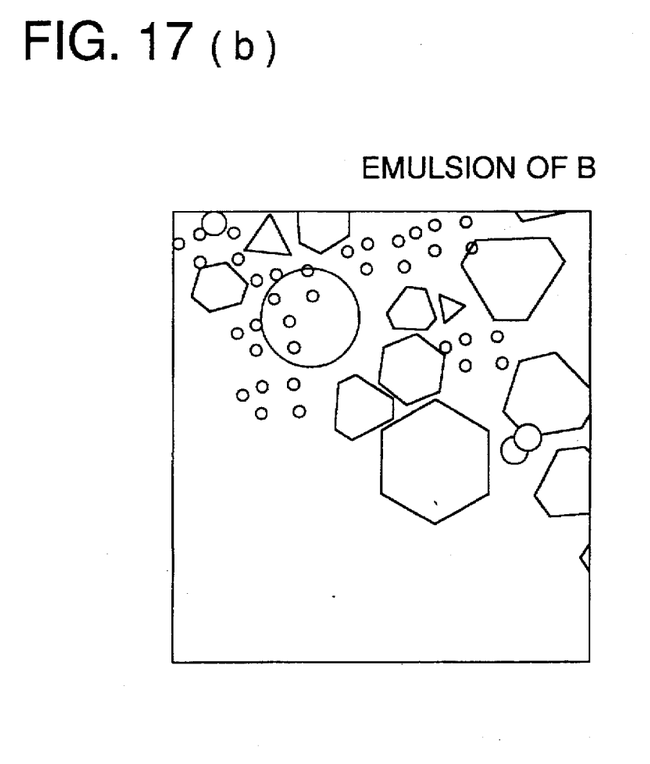

In normal production lots, the spectrum is shown by characteristic curve X in FIG. 16 after a predetermined period of time, however, in some production lots, the spectrum is shown by the characteristic curve Y in FIG. 16 at the same point of time, and the peak intensity is decreased when compared with the characteristic curve X. After the problem was investigated, the following causes are found: while tabular grains are included in normal silver halide emulsion as shown in FIG. 17(a), many smaller grains are included together with tabular grains in the emulsion having an abnormal spectrum as shown in FIG. 17(b). Accordingly, aging of the silver halide emulsion is stopped at this point of time, and the production process is repeated again from the adjustment stage of the silver halide grains. Accordingly, the adjustment process and other processes following that process, are carried out without any wasteful operation, resulting in minimum damage.

[EXAMPLE 3]

In systems in which the above-described sensitizing dye 1 and the following sensitizing dye 2 are used together, the following was found: when the sensitizing dye 2 is added after a predetermined period of time has passed after the addition of the sensitizing dye 1, the spectral sensitization ability is increased.

Figure 18:
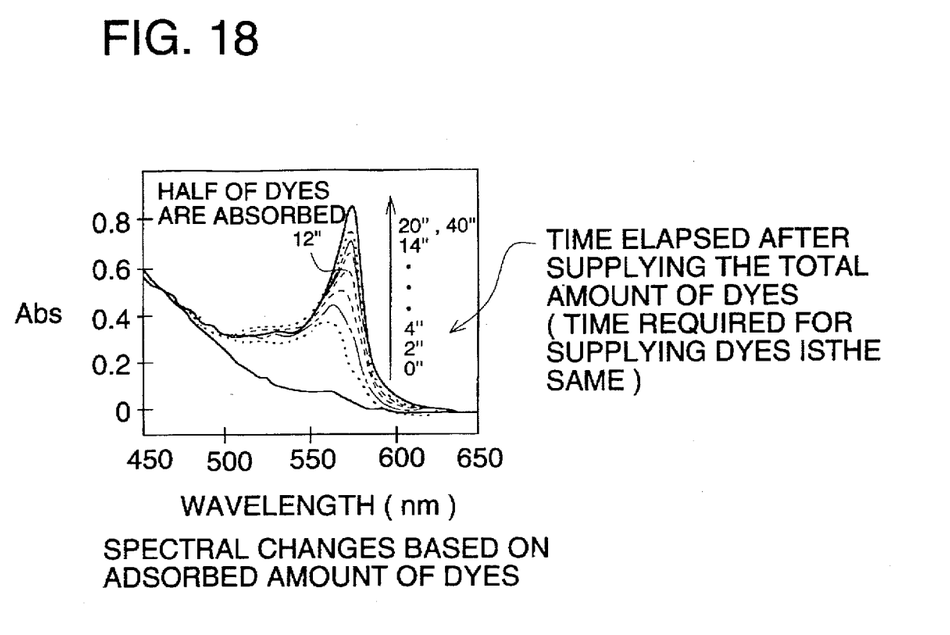
FIG. 18 is a view showing another diffuse reflectance spectra.

However, when the spectral sensitization (IIR) scale is changed, the optimum addition time of the sensitizing dye 2 changes each time, and a high sensitization processing method can not be realized in the level of process. However, when the present invention is used for determining the addition timing of the sensitizing dye, the following is found: when the sensitizing dye 2 is added when just half of the total addition amount of the sensitizing dye 1 is adsorbed as shown in FIG. 18, the spectral sensitization ability is most enhanced. When the emulsion production apparatus of the present invention is used, the spectral sensitization can be conducted, while the addition timing of the sensitizing dye depending on the difference of the IIR scale, is judged accurately every time. In this connection, the change of the adsorption amount of the sensitizing dye can be determined by Kubelka-Munk-conversion of the light absorption degree of the spectrum obtained by the measurement of the diffuse reflectance spectrum. (Refer to page 33 in "Spectrum Measurement and Spectrophotometer" written by Kazuo Shibata, issued by Kodan-Sha.)

As described above, in the invention, light is irradiated onto the liquid material, the reflected light by the liquid material is received, and the spectrum of the reflected light is measured in real-time, thereby data can be obtained without manually manipulating results of the experiment.

In the invention, the reflected light is the diffusive reflection light. For example, the diffusive reflection light reflected by the measuring object is received and measured without receiving the reflected light from the light transmitting window provided in the sensor unit, therefore, the spectrum analysis can be assuredly conducted.

In the invention, the liquid material is photosensitive material in the spectral sensitization process, and the behavior of the emulsion in the spectral sensitization process can be recognized, which had not been conducted conventionally.

In the invention, the light projecting means and the light receiving means are composed of optical fibers, and these optical fibers are provided in the sensor unit arranged in the case having a light transmitting window. Therefore, the sensor unit is caused to be in direct contact with the liquid material in the liquid material production line. Thereby, it is not necessary to sample a portion of the liquid sample, and simple and real-time measurements can be performed.

In the invention, the light projecting means and the light receiving means are composed of a plurality of optical fibers, and the optical fibers are provided in the sensor unit arranged in the case having a light transmitting window. Accordingly, when the sensor unit is caused to be in direct contact with the liquid material, in a measuring system which samples liquid material from the liquid material production line, it is not necessary to sample a portion of the liquid sample, and thereby also, simple and real-time measurements can be performed.

In the invention, the optical fibers are arranged inside the sensor unit; distance "d" from the leading edge of the optical fiber to the contact portion of the light transmitting window, to which the central axis of the optical fibers are extended, is determined by the specific relational expression and is set; and the effective diameter of the optical fiber, the expanding angle of the luminous flux, the angle formed between the central axis of the optical fiber and the light transmitting window, and the distance from the leading edge of the optical fiber to the contact portion with the light transmitting window, to which the central axis of the optical fiber is extended, are set. Thereby, the overall size of the sensor unit can be reduced, and it is not necessary to sample a portion of the liquid sample, and further simple and real-time measurements can be performed.

In the invention, the light transmitting window is formed of glass. Thereby, even when temperature of the liquid material, the spectrum of which is to be measured, is high, the window is prevented from softening by high temperature.

In the invention, when the adsorption condition of the sensitizing dye on silver halide grains is measured in the spectral sensitizing process of the photosensitive emulsion, the behavior of the emulsion in the spectral sensitizing process can be recognized.

The invention comprises the measuring sensor described above, and an addition means to add additive agents while continuously monitoring and controlling the adsorption condition of the sensitizing dye onto silver halide grains in the emulsion, obtained from the measuring sensor. Accordingly, when additive agents are added on-line while continuously monitoring and controlling the adsorption condition of the sensitizing dye, then, silver halide emulsions which are highly sensitive and excellent in storage stability can be produced, and the reproducibility of the spectral sensitization among production lots can be enhanced.

What is claimed is:

1. An apparatus for measuring spectrum of light reflected from a solution, comprising:

a sensor case on which a window is provided;

a light transmitting member provided on the window in such a construction that, when the window is immersed in the solution, the solution is prevented from entering in the case by the light transmitting member;

a light emitting member provided in the case so that light emitted from the light emitting member passes through the light transmitting member on the window and proceeds in the solution;

a light receiving member provided in the case so that first reflected light reflected from the solution returns into the case through the light transmitting member and is received by the light receiving member; and the light transmitting member, the light emitting member and the light receiving member arranged in such a positional relation that second reflected light which is emitted from the light emitting member and directly reflected by the light emitting member without proceeding in the solution, is not received by the light receiving member.

2. The apparatus of claim 1, further comprising a light source which is connected with the light emitting member and a spectrophotometer which is connected with the light receiving member so that the spectrum of light received by the light receiving member is measured by the spectrophotometer.

3. The apparatus of claim 2, wherein the first reflected light is diffused reflected light.

4. The apparatus of claim 2, wherein the solution is an emulsion which is processed in a vessel, and the window of the case is immersed in the solution in the vessel so that the spectrum of the first reflected light is measured while the solution is processed in the vessel.

5. The apparatus of claim 4, wherein the vessel comprises a sampling line in which the window of the container is immersed in the solution.

6. The apparatus of claim 4, wherein the emulsion is a photosensitive emulsion which is subjected to a spectral sensitivity increasing process in the vessel.

7. The apparatus of claim 6, wherein the photosensitive emulsion comprises silver halide particles and a dye for increasing a sensitivity of the silver halide particles is added in the photosensitive emulsion in the spectral sensitivity increasing process, and wherein a condition that the dye is adsorbed on the silver halide particles is measured from the spectrum.

8. The apparatus of claim 7, wherein the adsorbed condition is measured while the photosensitive emulsion is subjected to the spectral sensitivity increasing process and the addition of the dye in the photosensitive emulsion is controlled while the absorbing condition is measured.

9. The apparatus of claim 1, wherein the light emitting member and the light receiving member are constructed by optical fiber.

10. The apparatus of claim 9, wherein the optical fiber of the light emitting member having an optical axis is arranged so as to satisfy a following formula:

$$d \geq a/\sin\theta(((\cos\beta/\cos(\theta+\beta))-\cos\theta)$$

wherein "a" is a diameter of the optical fiber of the light emitting member, "$\theta$" is a diverging angle with which the light is diverged from the optical fiber, "d" is a distance along the optical axis between a tip end of the optical fiber and the light transmitting member, and "$\beta$" is a angle formed by the optical axis of the optical fiber and the light transmitting member.

11. The apparatus of claim 1, wherein each of the light emitting member and the light receiving member is constructed by plural pieces of optical fiber, and the plural pieces of optical fiber are made in a single body.

12. The apparatus of claim 1, wherein each of the light emitting member and the light receiving member is constructed by plural pieces of optical fiber, and the plural pieces of optical fiber of the light emitting member and the plural pieces of optical fiber of the light emitting member are made in a single body.

13. The apparatus of claim 12, wherein optical fiber of the light emitting member and optical fiber of the light receiving member are distributed one after another.

14. The apparatus of claim 1, wherein the light transmitting member is made of a glass.

15. The apparatus of claim 1, wherein a light absorbing member is provided on the light transmitting member so as not to cause the second reflected light.

16. The apparatus of claim 15, wherein the light absorbing member is a black color member.

* * * * *